United States Patent
Ruebusch et al.

[11] Patent Number: 6,136,303
[45] Date of Patent: Oct. 24, 2000

[54] AEROSOL PACKAGE COMPOSITIONS CONTAINING FLUORINATED HYDROCARBON PROPELLANTS

[75] Inventors: Nicholas Arthur Ruebusch, Ft. Thomas, Ky.; Scott Edward Smith; David Frederick Swaile, both of Cincinnati, Ohio

[73] Assignee: The Procter & Gamble Company, Cincinnati, Ohio

[21] Appl. No.: 09/523,081

[22] Filed: Mar. 10, 2000

Related U.S. Application Data

[63] Continuation of application No. 09/074,432, May 7, 1998, Pat. No. 6,045,784.

[51] Int. Cl.$^7$ ...................................................... A61K 7/32
[52] U.S. Cl. ................................ 424/65; 424/66; 424/67; 424/68; 424/400; 424/401
[58] Field of Search .................................. 424/65, 66, 67, 424/68, 400, 401

[56] References Cited

U.S. PATENT DOCUMENTS 3,725,540   4/1973   Wahl .......................................... 424/46

FOREIGN PATENT DOCUMENTS 1 362 495   8/1974   European Pat. Off. .
1 482 917   8/1977   European Pat. Off. .
1 534 861   12/1978  European Pat. Off. .

*Primary Examiner*—Shelley A. Dodson
*Attorney, Agent, or Firm*—William J. Winter

[57] ABSTRACT

Disclosed are anhydrous aerosol package compositions which comprise (a) a Lewis acid having a pKa of less than about 5.0; (b) from about 5% to about 95% by weight of a fluorinated hydrocarbon propellant; (c) a hydrogen bonded water source; and (d) a rust inhibition means. The aerosol package compositions are preferably anhydrous aerosol antiperspirants which comprise an antiperspirant active, a fluorinated hydrocarbon propellant such as 1,1-difluroethane, and a rust inhibition means, wherein the antiperspirant active acts as a Lewis acid and contains hydrogen bonded water. It was found that aerosol package compositions containing fluorinated hydrocarbons, a strong Lewis acid, and a hydrogen bonded water source are surprisingly susceptible to corrosion or rust formation of any metal surface within the package, unless a known or otherwise effective rust inhibition means is added to or used in association with the packaged aerosol composition.

21 Claims, No Drawings

AEROSOL PACKAGE COMPOSITIONS CONTAINING FLUORINATED HYDROCARBON PROPELLANTS

This application is a continuation of Ser. No. 09/074,432 filed May 7, 1998 now U.S. Pat. No. 6,045,784.

TECHNICAL FIELD

The present invention relates to aerosol package compositions which comprise a Lewis acid, a fluorinated hydrocarbon propellant, and means for inhibiting corrosion or rust of the aerosol package when the composition is packaged in a metal aerosol container.

BACKGROUND OF THE INVENTION

Packaged aerosol compositions are well known for use in a variety of consumer product areas, including application of personal care products such as hairsprays, hairstyling or conditioning gels or mousses, cosmetics, antiperspirants and deodorants, aftershave or shaving gels and creams, first aid sprays, and so forth. Other consumer product areas include household, industrial, or agricultural application.

All such aerosol products typically contain an active ingredient, a liquid carrier for the active ingredient, and a suitable propellant. The propellant is in the form of a compressed gas, typically a liquefiable gas, which acts to expel the liquid carrier and active ingredient from the aerosol package to the site of application. Examples of aerosol propellants include halogenated hydrocarbons such as fluorohydrocarbons and chlorofluorohydrocarbons, hydrocarbon gases such as butane and propane and dimethyl ethane, carbon dioxide, and nitrous oxide, and many others.

The use of many of these propellants, however, has been restricted for environmental or other safety concerns. The use of chlorofluorocarbons, for example, has been limited due to concerns that it contributes to depletion of the ozone layer of the upper atmosphere. By contrast, hydrocarbon propellants are not believed to be associated with ozone layer depletion and are now used extensively in aerosolized consumer products. Even the use of these hydrocarbon propellants, as well as other volatile organic compounds (VOC), are now being limited due to safety concerns associated with the release of large amounts of VOC's into the atmosphere from aerosolized consumer products.

Recently, fluorinated hydrocarbon propellants such as 1,1-difluoroethane have been used as a replacement for the more commonly used hydrocarbon propellants. It is believed that these fluorinated hydrocarbons are less harmful to the environment than most hydrocarbon propellants, and that the use of these fluorinated hydrocarbons allows for the formulation of aerosol products with reduced VOC content. These fluorinated hydrocarbons are especially useful in anhydrous antiperspirant and hairspray compositions. It has been found, however, that the use of these fluorinated hydrocarbon propellants can result in corrosion of the metal liner or surface within the aerosol container containing the propellant even when the composition is an anhydrous system that would not otherwise promote such corrosion. It has been found that corrosion of the metal container results in the visible appearance of rust on the inner surface of the container, which was very surprising given that the rust was first identified in a completely anhydrous system, and also given that comparable compositions containing hydrocarbon propellants do not have the same rust or corrosion problem.

It has also been discovered that this surprising rust or corrosion problem occurs in anhydrous systems when the fluorinated hydrocarbon is used in the presence of a strong Lewis acid having a pKa of less than about 5.0 and a source of hydrogen bonded water (i.e. bound water). For antiperspirant compositions, the aluminum and/or zirconium polymer salt acts as a strong Lewis acid that also contains hydrogen bonded water. It has been found, quiet surprisingly, that when fluorinated hydrocarbon propellants are used in such antiperspirant compositions that some rust formation can be noted on the inner surface of many of the metal aerosol packages containing such compositions.

It has now been discovered that this surprising rust formation problem in anhydrous aerosol compositions as described herein can be corrected by any known or otherwise effective rust inhibition means suitable for use in aerosol containers and suitable for use in consumer products.

In view of the foregoing, it is therefore an object of the present invention to provide an aerosol package composition containing fluorinated hydrocarbons which do not provide for canister corrosion or rust formation. It is yet another object of the present invention to provide an anhydrous aerosol package composition which contains a fluorinated hydrocarbon, a Lewis acid, and a source of hydrogen bonded water, wherein the components of the composition do not react and cause canister corrosion or rust formation. It is yet another object of the present invention to provide an anhydrous aerosol antiperspirant package composition which contains fluorinated hydrocarbons and an aluminum and/or zirconium polymer salt, that do not react and result in the corrosion of a metal aerosol container. It is yet another object of the present invention to provide an anhydrous aerosol package composition wherein the inner surface of the aerosol container has been treated with a rust inhibitive material.

SUMMARY OF THE INVENTION

The present invention is directed to aerosol package compositions which comprise (a) a Lewis acid having a pKa of less than about 5.0; (b) from about 5% of about 95% by weight of a fluorinated hydrocarbon propellant; (c) a hydrogen bonded water source; and (d) a rust inhibition means.

The present invention is also directed to aerosol antiperspirant package composition which comprise (a) from about 0.5% to about 60% by weight of an antiperspirant active; (b) from a bout 5% to about 95% by weight of a fluorinated hydrocarbon propellant; and (c) a rust inhibition means.

It has been found that the use of fluorinated hydrocarbon propellants in aerosol package compositions containing an active ingredient can result in corrosion of the aerosol container when within the container are a strong Lewis acid and a bound water source.

DETAILED DESCRIPTION OF THE INVENTION

The aerosol package compositions of the present invention are anhydrous systems which comprise a Lewis acid, a fluorinated hydrocarbon propellant, and a means for inhibiting corrosion of the aerosol package when the composition is packaged into a metal aerosol container.

The term "ambient conditions" as used herein refer to surrounding conditions at about one atmosphere of pressure, about 50% relative humidity, and about 25° C.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

The aerosol package compositions of the present invention can comprise, consist of, or consist essentially of the essential elements and limitations of the invention described herein, as well as any of the additional or optional ingredients, components, or limitations described herein.

Lewis Acid

The aerosol package compositions of the present invention comprise a Lewis acid having a pKa value of less than about 5.0, preferably less than about 4.5. These Lewis acids for use in the composition are relatively strong acids and are those which are capable of interacting with the hydrogen bonded water component of the aerosol composition to result in the formation of a hydrated metal ion complex.

The aerosol package compositions of the present invention comprise the Lewis acid at any of a variety of concentrations depending upon the desired product form, the chemical and physical nature of the Lewis acid, the other formulation ingredients, and so forth. The concentration of most Lewis acids will typically range from about 0.5% to about 90%, preferably from about 5% to about 60%, more preferably from about 5% to about 35%, by weight of the composition. The Lewis acid is preferably included in the composition as a hydrated metal ion complex wherein the weight percentage of the metal complex is calculated on an anhydrous metal salt basis exclusive of water and any complexing agents such as glycine, glycine salts, or other complexing agents. Most preferred are Lewis acids in the form of antiperspirant zirconium and/or aluminum salts having hydrogen bonded water.

It has been found that strong Lewis acids for use in the anhydrous aerosol package compositions can react with a fluorinated hydrocarbon propellant in the presence of hydrogen bonded water, even though the composition still contains no free or unbound water, and result in canister corrosion when the aerosol package is a metal aerosol container. This interaction of a strong Lewis acid with the propellant can occur when the Lewis acid is included in the composition as a hydrated metal ion complex or when the Lewis acid is allowed to react with the propellant in the presence of another source of hydrogen bonded water, i.e. bound water.

The strong Lewis acid for use in the aerosol package compositions include any compound, composition or other material that can be identified as a Lewis acid, provided that the Lewis acid is sufficiently strong and has a pKa value of less than about 5.0. These strong Lewis acids are capable of reacting with water and forming a hydrated metal ion complex, e.g., aluminum and/or zirconium antiperspirant salts. Preferably, the strong Lewis acid is present in the form of an antiperspirant active, nonlimiting examples of which include the astringent metallic salts, especially the inorganic and organic salts of aluminum, zirconium and zinc, as well as mixtures thereof. Particularly preferred are the aluminum and zirconium salts, such as aluminum halides, aluminum chlorohydrate, aluminum hydroxyhalides, zirconyl oxyhalides, zirconyl hydroxyhalides, and mixtures thereof.

Preferred aluminum salts for use in the aerosol package compositions, which also represent a strong Lewis acid and a hydrogen bonded water source as defined herein, include those which conform to the formula:

$$Al_2(OH)_aCl_b.xH_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the aerosol package compositions, which also represent a strong Lewis acid and a hydrogen bonded water source as defined herein, include those which conform to the formula:

$$ZrO(OH)_{2-a}Cl_a.xH_2O$$

wherein a is from about 0 to about2; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978, all of which are incorporated herein by reference.

Concentration of the preferred zirconiums and/or aluminum salts in the composition preferably range from about 0.5% to about 60%, more preferably from about 5% to about 26%, even more preferably from about 9% to about 15% by weight of the composition. Aluminum salts are most preferred.

Propellant

The aerosol package compositions of the present invention comprises a fluorinated hydrocarbon propellant that may react with the strong Lewis acid in the presence of hydrogen bonded water as described hereinabove. This interaction of the fluorinated propellant, strong Lewis acid, and hydrogen bonded water is believed to ultimately result in the formation of rust on any metal surface within the aerosol package.

The total concentration of the fluorinated hydrocarbon propellant, or the total concentration of any propellant combination comprising fluorinated hydrocarbon propellant, in the aerosol package composition can include one or more fluorinated hydrocarbon propellants, the total propellant concentration typically ranging from about 5% to about 95%, preferably from about 15% to about 60%, more preferably from about 40% to about 60%, by weight of the composition. The preferred fluorinated hydrocarbon propellant is 1,1-difluorethane (Hydrofluorocarbon 152A) supplied as Dymel 152A by Dupont.

The aerosol package composition may further comprise other aerosol propellants for use in combination with the fluorinated hydrocarbon propellant described herein. Suitable optional propellants include any propellant that is known or otherwise effective for use in consumer aerosol products, and which is otherwise compatible with the essential and any optional ingredients in the aerosol composition. Nonlimiting examples of optional propellants include hydrocarbon propellants such as propane, butane, dimethyl ether, and isobutane, nitrouos oxide, carbon dioxide, and other halognated hydrocarbons such as triclorofluormethane, diclorodifluoromethane, diclorotetrafluorethane and trichlorotrifluoroethane, trichlorotetrafluoroethane, monochlorodifluoromethane, and mixtures thereof.

Rust Inhibition Means

The aerosol package compositions of the present invention comprises a means for inhibiting corrosion or rust of any metal surface or liner within the aerosol container. The rust inhibition means includes any known or otherwise effective means for controlling or eliminating the formation of rust or corrosion on metal surfaces within an aerosol or other metal-containing package or surface.

Preferred rust inhibition means are those which can control or prevent the interaction of the Lewis acid, fluorinated hydrocarbon propellant, and hydrogen bonded water to thus inhibit the formation of any corrosion material from such an interaction, or otherwise inhibit the formation of conditions that promote corrosion of any metal surface of liner within the aerosol container. Also preferred are any known or otherwise effective rust inhibition means in the form of a chemical or physical barrier that prevents or minimizes contact between any metal surface within the aerosol package and the aerosol composition container therein.

Preferred rust inhibition means include 1) the use of inhibitors that minimize the interaction of the Lewis acid, the fluorinated hydrocarbon propellant, and hydrogen bonded water, 2) the use of scavenging and/or sequestering agents to effectively bind, neutralize or otherwise inactivate any corrosive materials resulting from the interaction of the Lewis acid, fluorinated hydrocarbon propellant, and hydrogen bonded water. Less preferred are those rust inhibition means that provide a chemical or physical barrier between the interacting materials and any metal surface within the aerosol package, an example of which involves the treatment of the metal surfaces within the package with a rust inhibitive material to provide a barrier between the inner surface and the corrosive material.

Nonlimiting examples of rust inhibition means which minimize the interaction of the Lewis acid, fluorinated hydrocarbon, and hydrogen bonded water include the use of a water-soluble barrier that interacts with and coats the Lewis acid, coating the Lewis acid with a water-insoluble polar solvent, and the use of a solvent in the aerosol composition that is immiscible with the fluorinated hydrocarbon propellant. Suitable nonlimiting examples of water-soluble barriers for interaction with and coating of the Lewis acid include materials such as lechtin, carbohydrates, dextrin, and mixtures thereof. Specific nonlimiting examples of suitable water-insoluble polar solvents for interaction with and coating of the Lewis acid include compounds such as butyl stearate, isopropyl palmitate, dimethicone copolyol, and mixtures thereof. Suitable nonlimiting examples of solvents that are immiscible with the fluorinated hydrocarbon propellant and that can be added to the aerosol composition include mineral oil, polydecene, and similar other materials. Particularly preferred is the use of solvents that are immiscible with the fluorinated hydrocarbon propellant.

Examples of rust inhibition means that effectively bind, neutralize or otherwise inactivate any corrosive materials resulting from the interaction of the Lewis acid, fluorinated hydrocarbon propellant, and hydrogen bonded water, include the use of any known or otherwise effective fluoride scavenging agent such as calcium chloride, calcium carbonate, and mixtures thereof. Examples of suitable sequestering agents include any known or otherwise effective material for chelating fluoride or other similar cation, some examples of which include chelating amines such as ethylene diamine-N,N,N',N'-tetracetic acid (EDTA), acetylacetone, nitrilotriacetic acid, oxalate, citric acid, 1,2-diaminocyclohexane-N,N,N',N'-tetracetic acid, 4,5-dihydroxybenzene-1,3-disulfonic acid, pyrocatechol-3,5-disulfonate, calicylic acid, 5-sulfosalicyclic acid, xylenol orange, aurintricarboxylic acid, 2,2'-pyridyl ethylene diamine, glycine, 8-hydroxyquinoline-5-sulfonic acid, lactic acid, 1,10-phenanthroline, pyridine, pyridine-2,6-dicarboxylic acid, 8-quinolinol, succinic acid, tartaric acid, thioglycolic acid, 1,1,1-trifluoro-3,2'-thenolyacetone, triethylene tetramine, and mixtures thereof.

Alternatively, the inner surface of any metal within the aerosol package, typically the inner metal surface or liner within the aerosol package, can be treated or coated with any material suitable for preventing or minimizing contact between such metal surface and any potentially corrosive material or combination of materials within the aerosol composition. Preferably, the inner surface of the aerosol package is impregnated or coated with rust inhibitive materials such as thermoplastic resins or other synthetic resin materials. Nonlimiting examples of suitable thermoplastic resins include polyethylene, polypropylene, a copolymer of modified resin of polyethylene and polypropylene, and mixtures thereof. Nonlimiting examples of other synthetic resin coating materials include polyester resin coatings, aminoalkyl resin coatings, amide resin coatings, imide resin coatings, acrylic resin coatings, phenolic resin coatings, vinyl chloride resin coatings, epoxy resin coatings, polyurethane resin coatings, silicone resin coatings, and mixtures of these coatings.

Other suitable means for providing a barrier between the aerosol metal surface and the contained composition includes increasing the tin plate coating weight of the inner metal surface to above about 2.4 grams/m$^2$ (grams of tin plating per inner surface area), preferably above about 2.8 to about 5.6 grams/m$^2$.

Hydrogen Bonded Water

The aerosol package compositions of the present invention are anhydrous compositions that preferably comprise only hydrogen bonded water in an amount sufficient to promote interaction with the fluorinated hydrocarbon and Lewis acid components described herein. This hydrogen bonded water, also referred to herein as bound water, is typically present in relatively low concentrations and is in the form of water that is hydrogen bonded to the Lewis acid or other essential or optional material within the aerosol composition, or which is otherwise not free water. The term "hydrogen bonded water" as used herein therefore includes water that is hydrogen bonded to or otherwise trapped by a substrate, or which is otherwise not free water. Examples of materials containing hydrogen bonded water for use in the composition are antiperspirant actives such as aluminum and/or zirconium polymer salts.

The aerosol package compositions of the present invention are therefore anhydrous compositions which comprise little or no unbound or free water. In this context, the term "anhydrous" means that the aerosol composition of the present invention contains less than about 5%, preferably less than about 3%, more preferably less than about 1%, most preferably zero percent, by weight of unbound water. In this context, the term "unbound water" specifically excludes hydrogen bonded water as described herein, and therefore only includes free or unbound water within the composition.

The aerosol package composition most preferably contains zero percent by weight of unbound water. For those aerosol embodiments containing some but lower concentrations, i.e. above zero percent but less than about 5% by weight of water, it is highly preferred that the small amounts of unbound water have a relatively neutral pH to avoid reaction with the fluorinated hydrocarbon. This can be accomplished by a number of means including the use of buffering agents, barriers between the Lewis acid and the unbound water, and other means well known for use in controlling formulation pH values.

Optional Liquid Carrier

The aerosol package compositions of the present invention may further comprise an optional liquid carrier suitable for application to human hair or skin, preferably a hydrophobic liquid carrier. The liquid carrier may provide emolliency benefits, acts as a diluent for the strong Lewis acid component within the aerosol package composition, and facilitates the uniform distribution of any active ingredients or other materials within the composition onto the skin, e.g., antiperspirant active.

The optional liquid carrier can be included in the aerosol package compositions as an individual liquid carrier or a combination of liquid carriers, the total concentration of the liquid carrier typically ranging from about 15% to about 55%, preferably from about 20% to about 45%, more preferably from about 25% to about 35%, by weight of the composition.

The optional liquid carrier for use herein include volatile silicones, nonvolatile silicones, functionalized silicones, volatile organics, nonvolatile organics, and mixtures thereof. As used herein the term "volatile" refers to those liquid carrier materials which have a vapor pressure under ambient conditions of at least about 0.2 mm of Hg. Conversely, the term "nonvolatile" refers to those liquid carrier materials which have vapor pressure of less than about 0.2 mm of Hg under ambient conditions. The aerosol package composition preferably comprises a combination of volatile and nonvolatile silicone materials, more preferably a combination of volatile and nonvolatile silicone liquid carriers, examples of which are described in U.S. Pat. No. 5,156,834 (Beckmeyer et al.), which description is incorporated herein by reference.

Specific examples of suitable volatile silicone liquid carriers include cyclic, linear or branched chain silicones having the requisite volatility defined herein. Nonlimiting examples of suitable volatile silicones are described in Todd et al., "Volatile Silicone Fluids for Cosmetics", Cosmetics and Toiletries, 91:27–32 (1976), which descriptions are incorporated herein by reference. Preferred among these volatile silicones are the cyclic silicones having from about 3 to about 7, more preferably from about 4 to about 5, silicone atoms. Most preferably are those which conform to the formula:

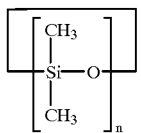

wherein n is from about 3 to about 7, preferably from about 4 to about 5, most preferably 5. These volatile cyclic silicones generally have a viscosity value of less than about 10 centistokes. All viscosity values described herein are measured or determined under ambient conditions, unless otherwise specified. Suitable volatile silicones for use herein include, but are not limited to, Cyclomethicone D-5 (commercially available from G. E. Silicones); Dow Corning 344, and Dow Corning 345 (commercially available from Dow Corning Corp.); GE7207, GE7158 and Silicone Fluids SF-1202 and SF-1173 (available from General Electric Co.); SWS-03314, SWS-03400, F-222, F-223, F-250, F-251 (available from SWS Silicones Corp.); Volatile Silicones 7158, 7207, 7349 (available from Union Carbide); Masil SF-V (available from Mazer); and combinations thereof.

Optional liquid carriers may also include a non-volatile silicone carrier other than or in addition to the volatile silicone carriers described hereinbefore. These non-volatile silicone carriers are preferably linear silicones which include, but are not limited to, those which conform to either of the formulas:

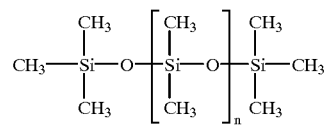

or

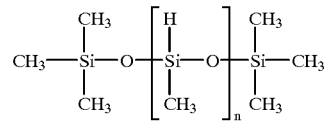

wherein n is greater than or equal to 1. These linear silicone materials will generally have viscosity values of up to about 100,000 centistoke, preferably less than about 500 centistoke, more preferably from about 1 centistoke to about 200 centistoke, even more preferably from about 1 centistoke to about 50 centistoke, as measured under ambient conditions. Examples of non-volatile, linear silicones suitable for use in the aerosol compositions include, but are not limited to, Dow Corning 200, hexamethyldisiloxane, Rhodorsil Oils 70047 available from Rhone-Poulenc, Masil SF Fluid available from Mazer, Dow Corning 225, Dow Corning 1732, Dow Corning 5732, Dow Corning 5750 (available from Dow Corning Corp.); SF-96, SF-1066 and SF18(350) Silicone Fluids (available from G. E. Silicones); Velvasil and Viscasil (available from General Electric Co.); and Silicone L-45, Silicone L-531 (available from Union Carbide), and Siloxane F-221 and Silicone Fluid SWS-101 (available from SWS Silicones).

Other optional liquid carriers include modified or organofunctional silicone carriers such as polyalkylsiloxanes, polyalkylarylsiloxanes, polyestersiloxanes, polyethersiloxane copolymers, polyfluorosiloxanes, polyaminosiloxanes, and combinations thereof. These modified silicone carriers are typically liquid under ambient conditions, and have a preferred viscosity of less than about 100,000 centistokes, more preferably less than about 500 centistokes, even more preferably from about 1 centistoke to about 50 centistokes, and most more preferably from about 1 centistoke to about 20 centistokes. These modified silicone carriers are generally known in the chemical arts, some examples of which are described in 1 *Cosmetics, Science and Technology*, 27–104 (M. Galsam and E. Sagarin ed. 1972); U.S. Pat. No. 4,202,879, issued to Shelton on May 13, 1980; U.S. Pat. No. 5,069,897, issued to Orr on Dec. 3, 1991; which descriptions are incorporated herein by reference.

Other optional liquid carriers include volatile, non-polar organic solvents such as isohexadecane, isododecane, various other hydrocarbon oils, and combinations thereof. In this context, the term "nonpolar" refers to those solvents having a solubility parameter of less than 8.0 $(cal/cm^3)^{0.5}$, preferably from about 5.0 $(cal/cm^3)^{0.5}$ to less than 8.0 $(cal/cm^3)^{0.5}$, more preferably from 6.0 $(cal/cm^3)^{0.5}$ to about 7.60 $(cal/cm^3)^{0.5}$.

Suitable volatile nonpolar solvents are those solvents have the above-described vapor pressure and solubility parameters, which can also include hydrocarbons, esters, amides, and ethers having the requisite vapor pressure and solubility parameter, Preferred are nonpolar hydrocarbon solvents which can be cyclic, branched or chain configurations, most preferably branched chain hydrocarbons.

Preferred volatile nonpolar solvents are the branched chain hydrocarbons having the requisite vapor pressure and solubility parameter and having from about 4 to about 30 carbon atoms, preferably from about 4 to about 20 carbon atoms, more preferably from about 6 to about 20 carbon atoms. Specific nonlimiting examples of these nonpolar volatile solvents include the isoparaffins available from Exxon Chemical Company, Baytown, Tex. U.S.A., as Isopar M (C13-C14 isoparaffin), Isopar C (C7-C8 Isoparaffin), C8-C9 Isoparaffin (Isopar E), Isopar G (C10-11 Isoparaffin), Isopar L (C11-C13 Isoparaffin) and Isopar H (C11-C12 Isoparaffin). Other nonlimiting examples of suitable branched chain hydrocarbons include Permethyl 99A (isododecane), Permethyl 102A (isoeicosane), Permethyl 101A (isohexadecane), and combinations thereof. The Permethyl series are available from Preperse, Inc., South Plainfield, N.J., U.S.A. Other nonlimiting examples of suitable branched chain hydrocarbons include petroleum distillates such as those available from Phillips Chemical as Soltrol 130, Soltrol 170, and those available from Shell as Shell Sol 70,-71, and -2033, and combinations thereof.

Nonlimiting examples of other suitable nonpolar volatile solvents include dibutyl adipate, diisopropyladipate, dodecane, octane, decane and combinations thereof, and the Norpar series of paraffins available from Exxon Chemical Company as Norpar 12, -13, and -15. Yet another example includes C11-C15 alkanes/cycloalkanes available from Exxon as Exxsol D80.

Other optional liquid carriers include nonvolatile, polar organic solvents such as mono and polyhydric alcohols, fatty mono and polyhydric alcohols, fatty acids, esters of mono and dibasic carboxylic acids with mono and polyhydric alcohols, polyoxyethylenes, polyoxypropylenes, polyalkoxylates ethers of alcohols, and combinations thereof. Preferably such optional liquid carriers are water-immiscible liquids under ambient conditions. Specific nonlimiting examples of such solvents include propyleneglycol monoisostearate; PPG-3 myristyl ether; PEG-8; 1,2 pentanediol, PPG-14 butylether, dimethyl isosorbide, isopropyl myristate, ethyl laurate, isopropyl palmitate, isopropyl behenate, decyl acetate, behenyl butyrate, hexadecyl acetate, decyl decanoate, methyl oleate, lauryl laurate, dioctyladipate, and combinations thereof. Other suitable water-immiscible, polar organic liquid carriers or solvents for use herein are described in Cosmetics, Science, and Technology, Vol 1, 27–104, edited by Balsam and Sagarin (1972); U.S. Pat. No. 4,202,879 issued to Shelton on May 13, 1980; U.S. Pat. No. 4,816,261 issued to Luebbe et al. on Mar. 28, 1989; U.S. Pat. No. 3,968,203 issued to Spitzer et al. on Jul. 6, 1976; and U.S. Pat. No. 3,752,540 issued to Wahl on Apr. 13, 1973; and U.S. Pat. No. 3,959,459, issued to Curry on May 25, 1976, which descriptions are incorporated herein by reference.

Optional Suspending Agent

The aerosol package compositions of the present invention may further comprise a suspending or bulking agent to help suspend any dispersed solids or liquids within the composition which is most typically in liquid form. Suitable suspending agents include any material known or otherwise effective in providing suspending or bulking properties to the composition, or which otherwise provide the desired viscosity to the final product form. These suspending agents include inorganic particulates such as clays or silicas, or combinations thereof.

Suitable optional suspending agents for use in the aerosol package composition include particulate suspending or thickening agents such as clays and colloidal pyrogenic silica pigments. Other known or otherwise effective particulate suspending agents can likewise be used in the aerosol package composition. Concentrations of optional particulate suspending agents preferably range from about 0.05% to about 3%, more preferably from about 0.2% to about 2%, even more preferably from about 0.5% to about 1% by weight of the aerosol composition.

Suitable colloidal pyrogenic silica pigments include Cab-O-Sil®, a submicroscopic particulated pyrogenic silica. Silicas are not preferred for use herein but can be utilized at concentrations of from about 0.05% to about 3% by weight of the composition.

Suitable clay suspending agents include montmorillonite clays, examples of which include bentonites, hectorites, and colloidal magnesium aluminum silicates. These and other clay suspending agents are preferably hydrophobically treated, and when so treated will generally be used in combination with a clay activator. Non-limiting examples of suitable clay activators include propylene carbonate, ethanol, and combinations thereof. The amount of clay activator will typically range from about 25% to about 75%, more typically from about 40% to about 60%, by weight of the clay. Propylene carbonate is the preferred clay activator and is typically included in the composition at a weight ratio of suspending agent to activator of from about 1:0.33 to about 1:1.

Preferred optional clay suspending agents include hydrophobic bentonites available under the trade name Bentone®. Suitable nonlimiting examples of suitable Bentones include Bentone 38, Bentone 34, Bentone 27, Bentone 14, Bentone LT, all of which have a particle size of below about 5 microns and are commercially available from NL Industries, Inc.

Other Optional Components

The aerosol package compositions of the present invention may further comprise other optional components known or otherwise effective for use in aerosolized antiperspirant or other personal care products, provided that the optional components are physically and chemically compatible with the essential component described herein, or do not otherwise unduly impair product stability, aesthetics or performance.

Nonlimiting examples of optional ingredients include preservatives, bactericides, perfumes, coloring agents, cosmetics, fillers, thickeners, allantoin, dyes, antisyneresis agents, wash-off aids, and other similar materials. The concentration of such optional ingredients generally ranges from about 0.01% to about 20% by weight of the composition.

The aerosol package composition may further comprise an active ingredient which may be added to or used in place of any antiperspirant active materials in the composition. Nonlimiting examples of such active ingredients include emollients, pharmaceutical actives, antifungal or other suitable antimicrobial agent, sun screens, deodorant perfumes, deodorant antimicrobials such as triclosan or triclocarbon or other similar materials, and combinations thereof.

Method of Manufacture

The aerosol package compositions of the present invention may be prepared by any known or otherwise effective technique, suitable for making and formulating an aerosol package composition, provided that the composition also has a means for inhibiting corrosion or rust of any metal surface or liner within the aerosol container.

Methods for preparing the aerosol package compositions of the present invention include conventional formulation and mixing techniques for aerosol formulations. Suitable methods include the formation of an aerosol concentrate by dispersing a suspending agent and activator in a liquid carrier. The dispersion is stored until it thickens due to swelling of the suspending agent. For antiperspirant aerosols, the antiperspirant active is then added with mixing. The mixture is then homogenized by the use of a Gifford-Wood shearing type homogenizer until a gel is formed and the desired viscosity is obtained. The gel constitutes the aerosol concentrate. The aerosol concentrate is then packaged into a suitable container such as a metal aerosol container.

The aerosol composition of the present invention can be contained or dispensed in any known or otherwise effective aerosol container or delivery system. All such containers or delivery systems should be compatible with the essential and any selected optional ingredients of the aerosol composition of the present invention.

Preferably, the aerosol composition is packaged in a pressurized aerosol container by combining the aerosol concentrate with a fluorinated hydrocarbon propellant such as 1,1-difluoroethane at a concentrate:propellant weight ratio of from about 0.5:1 to about 2.3:1.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified concentrations are weight-weight percents, unless otherwise specified.

Example 1

The composition described below is an anhydrous antiperspirant composition packaged within a metal aerosolized canister. The composition contains hydrogen bonded water associated with the antiperspirant active and contains no free or unbound water. The antiperspirant active acts as a strong Lewis acid that has both hydrogen bonded water and a pKa value of less than about 5.0. The aerosol package also contains a rust inhibition means in the form of a barrier surface or liner (epoxy-phenolic resin) within the aerosol package that prevents corrosion of the metal inner surface of the package.

| Antiperspirant Concentrate | |
|---|---|
| INGREDIENT | WEIGHT % |
| Dimethicone/Cyclomethicone Blend | 53.937 |
| Isopropyl Myristate | 12.562 |
| Quaternium-18 Hectorite | 2.513 |
| Aluminum Chlorohydrate | 30.151 |
| Propylene Carbonate | 0.837 |

The concentrate is prepared by combining the dimethicone/cyclomethicone blend with isopropyl myristate. The clay and propylene carbonate are then added and dispersed into the mixture. The resultant dispersion is stored for 15 to 20 minutes until it thickens to the desired velocity. The aluminum chlorohydrate (contains hydrogen bonded water) is then added with agitation. The resulting concentrate is homogenized in a Gifford-Wood shearing type homogenizer until a concentrate gel is formed having the desired viscosity. The homogenized concentrate is combined with 1,1-difluoroethane propellant at a concentrate to propellant weight ratio of about 0.66:1 in the epoxy-phenolic treated aerosol canister.

Examples 2–5

The compositions described below are aerosol antiperspirants that are packaged in a metal aerosol canister, and which contain a rust inhibition material which controls or prevents the development of rust or corrosion of the metal aerosol canister. The composition contains hydrogen bonded water associated with the antiperspirant active and contains no free or unbound water. The antiperspirant active acts as a strong Lewis acid that has both hydrogen bonded water and a pKa value of less than about 5.0. The aerosol compositions are formulated by conventional formulation and mixing techniques for making aerosol antiperspirant compositions.

| | Examples | | | |
|---|---|---|---|---|
| Ingredient | 2 | 3 | 4 | 5 |
| Aluminum Chlorohydrate | 12.00 | 12.00 | 12.00 | 12.00 |
| Cyclomethicone D5 | 19.67 | 15.67 | 19.67 | — |
| Butyl Stearate | — | — | — | 21.67 |
| Isopropyl Myristate | 5.00 | 5.00 | 5.00 | 5.00 |
| Quaterium 18 hectorite | 1.00 | 1.00 | 1.00 | 1.00 |
| Propylene Carbonate | 0.33 | 0.33 | 0.33 | 0.33 |
| Calcium Chloride Scavenging agent | — | — | 2.00 | — |
| EDTA Sequestering agent | 2.00 | — | — | — |
| Lechtin | — | 6.000 | — | — |
| 1,1-difluoroethane | 60.00 | 60.00 | 60.00 | 60.00 |

What is claimed is:

1. An anhydrous aerosol antiperspirant package composition comprising:

(a) from about 15% to about 26% by weight of an antiperspirant active;

(b) from about 5% to about 95% by weight of fluorinated hydrocarbon propellant; and (c) a rust inhibition means.

2. The composition of claim 1 wherein the composition contains zero percent by weight of free water and wherein the antiperspirant active contains hydrogen bonded water.

3. The composition of claim 2 wherein the fluorinated hydrogen propellant is 1,1-difluoroethane.

4. The composition of claim 3 wherein the antiperspirant active is selected from the group consisting of zirconium salt, aluminum salt, and combinations thereof.

5. The composition of claim 4 wherein the rust inhibition means comprises a means for inhibiting the interaction between the antiperspirant active and 1,1-difluoroethane.

6. The composition of claim 5 wherein the means for inhibiting the interaction of the antiperspirant active with 1,1-difluoroethane is selected from the group consisting of reacting the antiperspirant active with a water-soluble barrier, coating the antiperspirant active with a water-insoluble polar solvent, adding a solvent that is immiscible with 1,1-difluoroethane, and combinations thereof.

7. The composition of claim 4 wherein the rust inhibition means comprises a scavenging agent for any corrosive material that forms within the composition.

8. The composition of claim 4 wherein the rust inhibition means comprises a sequestering agent for any corrosive material that forms within the composition.

9. The composition of claim 4 wherein the rust inhibition means comprises a barrier coating within the package composition which prevents contact between the composition and an inner metal surface of the aerosol package.

10. The composition of claim 9 wherein the barrier coating is selected from the group consisting of polyethylene resins, polypropylene resins, copolymers of polyethylene resins, copolymers of polypropylene resins, polyester resins, aminoalkyl resins, acrylic resins, phenolic resins, amide resins, imide resins, vinyl chloride resins, epoxy resins, polyeurathane resins, silicone resins, and mixtures thereof.

11. An anhydrous aerosol package composition comprising:

(a) a Lewis acid having a pKa of less than about 5.0;

(b) from about 15% to about 60% by weight of a fluorinated hydrocarbon propellant;

(c) a hydrogen bonded water source; and (d) a rust inhibition means.

12. The composition of claim 11 wherein the composition contains zero percent by weight of free water.

13. The composition of claim 12 wherein the fluorinated hydrocarbon propellant is 1,1-difluoroethane.

14. The composition of claim 11 wherein the Lewis acid has a pKa value of less than about 4.5.

15. The composition of claim 12 wherein the rust inhibition means comprises a means for inhibiting the interaction between the Lewis acid, the hydrogen bonded water source, and the fluorinated hydrocarbon propellant.

16. The composition of claim 15 wherein the means for inhibiting the interaction between the Lewis acid, the hydrogen bonded water source, and the fluorinated hydrocarbon propellant is selected from the group consisting of reacting the Lewis acid with a water-soluble barrier, coating the Lewis acid with a water-insoluble polar solvent, adding a solvent that is immiscible with the fluorinated hydrocarbon propellant, and combinations thereof.

17. The composition of claim 12 wherein the rust inhibition means comprises a scavenging agent for any corrosive material that forms within the composition.

18. The composition of claim 12 wherein the rust inhibition means comprises a sequestering agent for any corrosive material that forms within the composition.

19. The composition of claim 12 wherein the rust inhibition means comprises a barrier coating within the package composition which prevents contact between the composition and an inner metal surface of the aerosol package.

20. The composition of claim 19 wherein the coating barrier is selected from the group consisting of polyethylene resins, polypropylene resins, copolymers of polyethylene resins, copolymers of polypropylene resins, polyester resins, aminoalkyl resins, amide resins, imide resins, acrylic resins, phenolic resins, vinyl chloride resins, epoxy resins, polyeurathane resins, silicone resins, and mixtures thereof.

21. The composition of claim 12 wherein aerosol package has an inner tin plate coating of at least about 2.4 grams/m$^2$.

* * * * *

UNITED STATES PATENT AND TRADEMARK OFFICE
CERTIFICATE OF CORRECTION

PATENT NO.   : 6,136,303
DATED        : October 24, 2000
INVENTOR(S)  : N. A. Ruebusch et al.

It is certified that error appears in the above-identified patent and that said Letters Patent is hereby corrected as shown below:

Column 2,
Line 44, "composition" should read -- compositions --.
Line 46, "a bout" should read -- about --.
Line 62, "refer" should read -- refers --.

Column 4,
Line 23, "about2" should read -- about 2 --.
Line 47, "comprises" should read -- comprise --.
Line 63, "difluorethane" should read -- difluoroethane --.

Column 5,
Line 8, "halognated" should read -- halogenated --.
Line 9, "triclorofluormethane" should read -- triclorofluoromethane --.
Lines 9-10, "diclorotetrafluorethane" should read -- diclorotetrafluoroethane --.
Line 16, "comprises" should read -- comprise --.
Line 25, "corrosion" should read -- corrosive --.
Line 27, "of" should read -- or --.
Line 32, "container" should read -- contained --.

Column 6,
Line 15, "calicylic" should read -- salicylic --.
Line 15, "sulfosalicyclic" should read -- sulfosalicylic --.
Line 32, "of" should read -- or --.

Column 7,
Line 13, "lower" should read -- low water --.

Column 8,
Line 59, after "L-45," insert the phrase -- Silicone L530, --.
Line 64, "polyalkylarylsiloxanes" should read -- polyalkyarylsiloxanes --.

UNITED STATES PATENT AND TRADEMARK OFFICE
CERTIFICATE OF CORRECTION

PATENT NO.     : 6,136,303
DATED          : October 24, 2000
INVENTOR(S)    : N. A. Ruebusch et al.

It is certified that error appears in the above-identified patent and that said Letters Patent is hereby corrected as shown below:

Column 9,
Line 8, "Galsam" should read -- Balsam --.
Line 20, "have" should read -- having --.

Column 10,
Line 58, "Suitable" should read -- Specific --.

Column 12,
Line 26, "velocity" should read -- viscosity --.

Column 13,
Line 7, "hydrogen" should read -- hydrocarbon --.

Signed and Sealed this

Twenty-fifth Day of November, 2003

JAMES E. ROGAN
*Director of the United States Patent and Trademark Office*